United States Patent
Crook

[11] Patent Number: 5,524,644
[45] Date of Patent: Jun. 11, 1996

[54] INCREMENTALLY ADJUSTABLE INCISION LINER AND RETRACTOR

[75] Inventor: Berwyn M. Crook, Yardley, Pa.

[73] Assignee: Medical Creative Technologies, Inc., Colmar, Pa.

[21] Appl. No.: 489,044

[22] Filed: Jun. 9, 1995

[51] Int. Cl.⁶ .................................................. A61F 13/00
[52] U.S. Cl. ........................ 128/888; 602/43; 602/63
[58] Field of Search ....................... 128/845, 846, 128/888; 602/42, 43, 50, 60, 63, 75, 901

[56] References Cited

U.S. PATENT DOCUMENTS

| | | |
|---|---|---|
| 1,810,466 | 6/1931 | Deutsch . |
| 2,305,289 | 12/1942 | Coburg . |
| 2,739,587 | 3/1956 | Scholl ........................ 602/63 |
| 3,111,943 | 11/1963 | Orndorff . |
| 3,332,417 | 7/1967 | Blanford et al. . |
| 3,347,226 | 10/1967 | Harrower . |
| 3,347,227 | 10/1967 | Harrower . |
| 3,397,692 | 8/1968 | Creager, Jr. . |
| 3,523,534 | 8/1970 | Nolan . |
| 3,841,332 | 10/1974 | Treacle . |
| 4,188,945 | 2/1980 | Wenander . |
| 4,553,537 | 11/1985 | Rosenberg . |
| 4,777,943 | 10/1988 | Chvapil . |
| 5,263,922 | 11/1993 | Sova ........................ 128/888 |
| 5,366,478 | 11/1994 | Brinkerhoff . |

FOREIGN PATENT DOCUMENTS

| | | | |
|---|---|---|---|
| 0165664 | 10/1955 | Australia ............... 602/901 |
| 0858821 | 1/1961 | United Kingdom ...... 602/901 |

*Primary Examiner*—Michael A. Brown
*Attorney, Agent, or Firm*—Howson and Howson

[57] ABSTRACT

An incrementally adjustable apparatus and method of use thereof for protecting an incised wound from exposure to bacterial and other harmful contaminants. A pair of resilient O-rings is connected to opposite ends of an impermeable pliable sleeve. One of the O-rings is formed to engage the inner edge of the wound with a portion of the sleeve above the wound capable of being rolled onto the other ring to draw the remaining sleeve portion contiguous with the sides of the wound. Flat surfaces on the other ring provide a gripping surface to turn the ring about its annular axis.

19 Claims, 1 Drawing Sheet

INCREMENTALLY ADJUSTABLE INCISION LINER AND RETRACTOR

FIELD OF THE INVENTION

The present invention relates generally to improvements in surgical wound protectors, and more particularly to an adjustable surgical wound protector for use in protecting incised cavity walls of various thicknesses from harmful contaminants during surgery.

BACKGROUND OF THE INVENTION

The sides of a wound during surgery are inherently susceptible to bacterial infection if touched by contaminated substances such as diseased body parts and fluids as they pass through the wound. Therefore extreme care must be exercised to insure that the exposed sides of an incision are completely covered by a material impervious to solids and fluids containing bacteria and other contaminants before surgery proceeds.

Various techniques have been used to insulate any incised tissue from exposure. One form of protection for relatively large incisions typically employs soft cotton sponges held against the sides of the wound by metal retractors to minimize contamination as well as to give the surgeon better access into the operating site. Another form of wound protector, particularly suitable for minimally invasive surgery, is disclosed in U.S. Pat. No. 3,347,227 to Harrower. It is constructed of a thin transparent and flexible sheet of material, impervious to bacteria and fluids, which is formed into a sleeve and secured at opposite ends to a pair of preformed resilient rings. One ring is squeezed into an oblong shape, inserted through the cavity wall, and allowed to expand to the preformed shape over the inside edge of the wound. The other ring overlaps the outside edge causing the sleeve to stretch into contiguous contact with the entire surface of the sides and inner and outer edges of the wound. To obtain a form-fitting contiguous contact with the sides of the wound, the circumference of both rings in their preformed shape must be slightly larger than that of the incision, and the extended length of the sleeve between the rings slightly greater than that of the wall thickness. To accommodate variations in wound sizes, this entails manufacturing and provisioning wound protectors in numerous combinations and permutations of both circumferences and lengths. U.S. Pat. No. 3,347,226 to Harrower describes an adjustable wound protector which reduces, to a degree, the number of sizes required. It requires a number of predetermined lengths similar to U.S. Pat. No. 3,347,227 supra, except the circumference of the wound protector is adjustable, before being installed in the wound, by the rings having telescoping ends, and the side of the sleeve having overlapping lengthwise edges. Any overlapping excess may be cut off. The rings have a maximum adjustable circumference slightly larger than that of the largest incision anticipated so that they are sure to overlap the inner and outer edges of the wound. However, a sleeve length must be selected which will closely conform to the wall thickness at the wound. Consequently, to insure a precise form fit for different size wounds, it is still necessary to provide numerous combinations of sleeve lengths and ring maximum adjustable circumferences.

OBJECTS OF THE INVENTION

Accordingly, it is an object of the present invention to provide a relatively low cost surgical wound protector of simplified design which can be easily installed in a wound and adjusted in place to form fit a wide range of cavity wall thicknesses for protection against harmful contaminants.

Another object of the invention is to provide an adjustable wound protector in which relatively few sizes are needed to form fit a wide range of incision sizes and cavity wall thicknesses.

Still another object of the invention is to provide a surgical wound protector which can be adjusted after being inserted in a wound to obtain contiguous contact with the sides of the cavity wall.

A still further object of the invention is to provide a method for adjusting the sleeve length of a wound protector after being inserted in an incision for securing the sleeve in contiguous contact with the sides of the incision.

SUMMARY OF THE INVENTION

More specifically, the adjustable surgical wound protector of the present invention comprises a flexible sleeve of thin material, impervious to solids and fluids containing bacteria and other contaminants, secured at opposite open ends around inner and outer preformed resilient O-rings, the outer one of which is of a particular construction. Installed in a wound, the O-rings expand around the inner and outer edges of the wound. Any portion of the sleeve extending above the wound is rolled onto the outer O-ring to draw the sleeve into contiguous contact with the sides of the wound. The outer O-ring in cross-section is generally circular with opposed flat sides in planes generally transverse to the extended length of the sleeve for restoring the outer O-ring to its preformed configuration when turned about the circumferencial axis of rotation of the ring. The flat sides also provide gripping surfaces for manually turning the outer O-ring with greater ease, especially when the sleeve or the surgeon's gloves are slippery. The wound protector may be constructed in a single sleeve length with different circumferences for accommodating a wide range of incision sizes and cavity wall thicknesses.

In practicing the invention, an adjustable surgical wound protector is selected having a circumference conforming to the size of the incision. After the inner O-ring of the protector is expanded around the inner edge of the wound, the sleeve portion above the wound is rolled onto the outer O-ring until it abuts the outer edge of the wound, and the remaining sleeve portion between the O-rings is thereby drawn into contiguous contact with the sides of the wound. Thus, a self-retaining protective barrier which fits the incision, which resists unrolling during surgery, and which is impervious to fluids and bacteria is provided.

BRIEF DESCRIPTION OF THE DRAWINGS

The foregoing and other objects, features, and advantages of the invention will become more apparent from the following description when taken in conjunction with the accompanying drawings wherein.

DESCRIPTION OF THE PREFERRED EMBODIMENT

Figure 1:
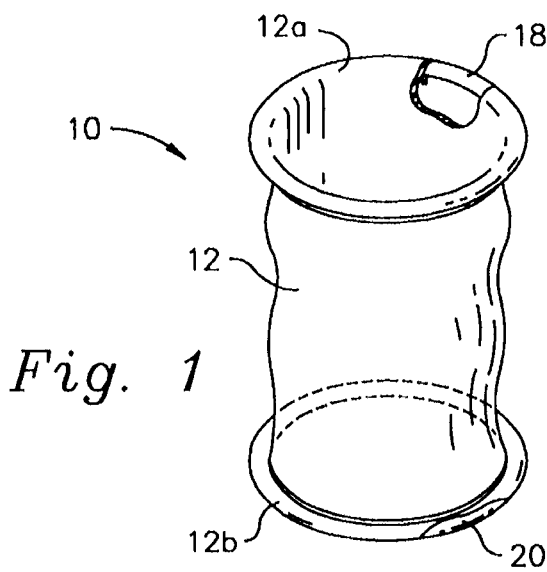
FIG. 1 is an isometric view of a preferred embodiment of an adjustable surgical wound protector according to the invention, in a fully extended state and with portions cut away.

Referring now to the drawings wherein like referenced characters denote like or corresponding parts throughout the several views, FIG. 1 illustrates an adjustable surgical wound protector, indicated generally by the numeral 10. The wound protector comprises a thin flexible tube, or sleeve, 12 of uniform circumference along its length. The sleeve is of a material impervious to solids and fluids containing bacteria and other harmful contaminants.

A conventional wound protector has an upper end portion 12a and a lower end portion 12b which are secured around their peripheries to resilient inner and outer O-rings, respectively. The problem with conventional wound protectors of this construction is their lack of easy adjustability and stability during surgery.

Figure 2:
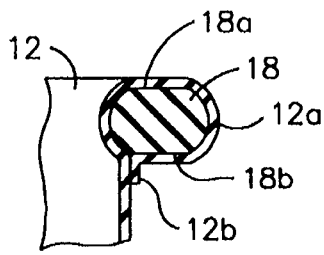
FIG. 2 is a view in longitudinal cross-section of an outer end of the wound protector of FIG. 1.
Figure 3:
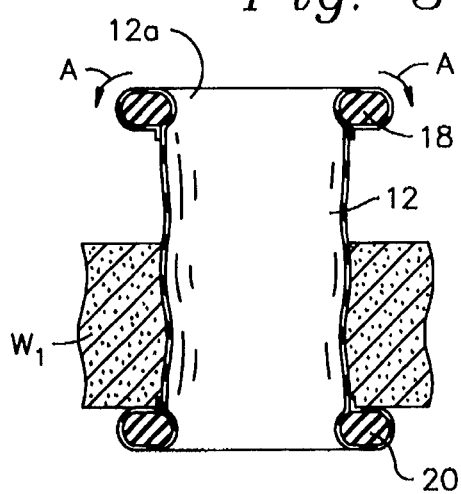
FIG. 3 is a schematic representation in longitudinal cross-section of the wound protector of FIG. 1 partially installed in a surgical wound.

In accordance with the present invention, the wound protector is adjustable axially in stable increments. To this end, as best seen in FIG. 2, the upper end portion 12a of the sleeve 12 wraps around outer O-ring 18 and terminates in an annular edge portion 12c sealed around the outer side of sleeve 12. At least one O-ring, such as the O-ring 18, is generally oblate in cross-section having opposed flat chordal side surfaces 18a and 18b which are transverse, i.e. substantially normal, to the sleeve central longitudinal axis defined by the extended length of sleeve 12, as shown in FIGS. 1–3. As shown, the chordal surfaces 18a and 18b are located equidistant from and on opposite sides of the centroid of the cross-section. The surfaces 18a and 18b provide surface means for purposes to be described.

Inner O-ring 20 is secured to lower end portion 12b in the same manner as O-ring 18, except the configuration in cross section is entirely circular. If desired, both O-rings may have the same cross-sectional shape as O-ring 18 to provide reversibility to the protector 10.

The oblate shape of the O-ring 18 provides stability in a plane perpendicular to the longitudinal axis of the sleeve 12 and provides an over center snap action when rolled about itself and the sleeve, thereby providing incremental shortening in predetermined increments and resistance to lengthening after shortening.

The materials and dimensions of wound protector 10 are selected to ensure stability of the wound protector when installed. A preferred plastic material suitable for sleeve 12 is a heat-sealable 3-mil polyolefin, such as Saranex® film 2050 manufactured by the Dow Chemical Company, produced in seamless tubular form or by a flat sheet in a cylindrical form with the meeting margins along the side overlapped and sealed. A nominal sleeve length suitable for minimally invasive surgery is typically around 150 mm. Sleeve diameters will vary according to wound length as will be discussed.

Outer and inner O-rings 18 and 20 are preferably preformed of an elastomeric medical grade material of sufficient hardness to retain O-rings 18 and 20 expanded in place around the inner and outer edges of the wound. The material must be compliant enough to allow O-ring 18 to be turned by the fingers over 180 degrees around its annular axis from the preformed configuration. For this purpose, urethane is the preferred elastomeric material. When the O-rings are of different configurations, the O-rings are preferably color-coded with different colors, such as white and blue, for aiding in recognizing the correct end of the protector to be inserted in the wound.

The inside circumferences of O-rings 18 and 20 generally correspond to the outside circumference of sleeve 12. By way of example, a urethane O-ring 18 for use with a sleeve 110 mm (4.33 inches) in diameter has a diameter across the transverse cross section of about 7.94 mm (5/16 inch) with a distance between parallel flat sides 18a and 18b of approximately 6.10 mm (0.240 inch). O-ring 20 has a diameter of its circular cross-section of about 7.94 mm (5/16 inch). Of course, the sizes of the O-rings and sleeves will vary according to wound size and wound wall thickness, and the personal preference of the surgeon will affect the choice of size for a particular surgical procedure.

The following table sets forth a preferred relation between incision length and sleeve and O-ring and sleeve diameters. It also sets forth the preferred cross-sectional diameters for each O-ring, it being understood that O-ring 18 has opposed flats and is, therefore, oblate and not circular in cross-section.

| Incision Length (mm) | Sleeve Diameter (mm) | O-Ring Cross Sectional Diameter (mm) |
| --- | --- | --- |
| 10 | 30 | 5.15 |
| 20 | 30 | 5.15 |
| 30 | 60 | 7.13 |
| 40 | 60 | 7.13 |
| 50 | 80 | 7.52 |
| 60 | 80 | 7.52 |
| 70 | 110 | 7.92 |
| 80 | 110 | 7.92 |
| 90 | 110 | 7.92 |
| 100 | 130 | 9.53 |
| 110 | 130 | 9.53 |
| 120 | 150 | 11.11 |
| 130 | 150 | 11.11 |
| 140 | 170 | 12.70 |
| 150 | 170 | 12.70 |
| 160 | 190 | 14.29 |
| 170 | 190 | 14.29 |
| 180 | 210 | 15.88 |
| 190 | 210 | 15.88 |
| 200 | 230 | 15.88 |

The durometers of the O-rings set forth in the above table should be in a range of 50 to 90 Shore A. The preferred material is urethane, but silicone could be used with some loss of stability after installation and adjustment. The best stability is achieved by using a material having a high modulus of elasticity with a ring, as manufactured, having a minimum of residual stresses and strains. The size of the flats affects both gripability for adjustment and stability after adjustment, since the larger the size of flats for a given O-ring cross-sectional diameter, the less stability that exists. By way of example, a preferred flat width for an O-ring having a cross-sectional diameter of 7.94 mm (5/16 inch) is 6.10 mm (0.240 inches). It is expected that with increasing diameters each flat width should increase proportionately based on a formula: $W = xD$ where W is the width of the flat; D is the diametrical cross-section of the O-ring; and x is a constant equal to 0.85 for a urethane ring having a hardness within the ranges stated.

Figure 4:
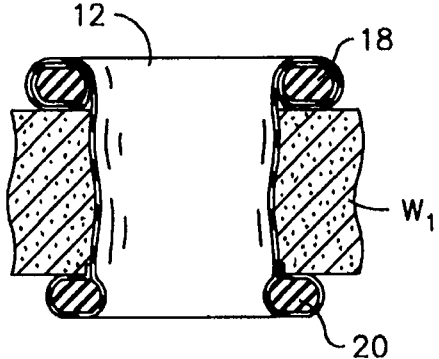
FIG. 4 schematically illustrates the wound protector of FIG. 3 completely installed in the surgical wound.

In using the adjustable surgical wound protector in a minimally invasive abdominal surgical procedure, the abdomen is routinely prepared with antiseptics and dried; the site for the incision is traced on the abdomen and covered with a surgical drape; and a muscle-split is made at the site through the peritoneum. As illustrated in FIG. 3, protector 10 is placed in wound W₁ by squeezing inner O-ring 20 into a tight oblong shape and inserting it lengthwise through the incision and letting it expand inside the peritoneum around the inner edge of the wound. Outer end portion 12a is gripped by the thumb and fingers at flat sides 18a and 18b of outer ring 18 (FIG. 2) and turned outwardly, in opposite directions shown by arrows A, rolling sleeve 12 on the O-ring until it abuts the outer edge of the wound W₁ as shown in FIG. 4. The part of sleeve 12 in the wound between O-rings 18 and 20 is thereby drawn into contiguous contact with the sides of wound W₁ to provide a self-retaining protective barrier during surgery which is impervious to contaminating solids and fluids. If desired, the protector 10 can also be pre-adjusted prior to insertion, or partially pre-adjusted.

Figure 5:
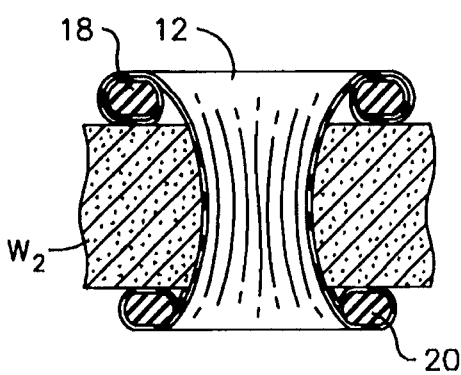
FIG. 5 schematically illustrates in longitudinal cross-section the wound protector of FIG. 1 completely installed in a smaller surgical wound but of the same wall thickness as the wound in FIGS. 3 and 4.
Figure 6:
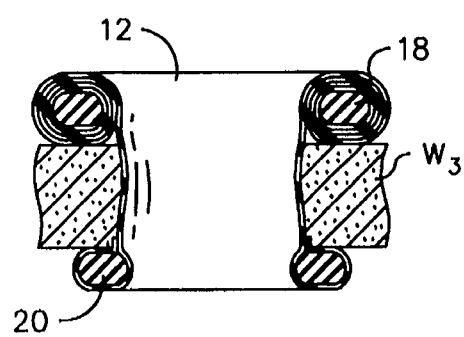
FIG. 6 schematically illustrates the wound protector of FIG. 1 completely installed in a wound of the same size as the wound in FIGS. 3 and 4, but of a thinner wall.

The adaptability of wound protector 10 to different wound sizes is clearly demonstrated in FIGS. 5 and 6. In FIG. 5, the wall thickness at wound W₂ is the same as in FIG. 3, but the length of the incision is somewhat less. Still, O-ring 18 is capable of drawing sleeve 12 tightly against the sides of the incision. Similarly, even though the size of wound W₃ in FIG. 6 is the same as in FIG. 3, and the wall thickness is considerably less, sleeve 18 can be drawn contiguous with the sides of wound W₃.

Some of the many advantages and novel features of the invention should now be readily apparent. For example, a relatively simple and inexpensive surgical wound protector is provided for protecting wounds from exposure to contamination. It can be quickly and easily installed in a wound and adjusted in place to form-fit a wide range of cavity wall thicknesses, and it stays in place after insertion. A fewer number of combinations of sizes of protectors are needed to accommodate a variety of incision sizes and cavity wall thicknesses.

It will be understood, of course, that various changes in the details, materials, steps and arrangement of parts, which have been described and illustrated in order to explain the nature of the invention, may be made by those skilled in the art without departing from the scope of the invention as expressed in the appended claims.

What is claimed is:

1. An adjustable surgical wound protector, comprising:

an elongate sleeve open at each of opposed ends thereof, said sleeve being made of a pliable material impervious to solid and fluid contaminants for inserting lengthwise in a wound;

an inner O-ring secured around one of said ends, said inner O-ring having a preformed resilient configuration for overlapping the inner edge of the wound and for squeezing into an oblong shape insertable with a lengthwise portion of the sleeve adjacent to said inner O-ring in the wound; and an outer O-ring secured around the other of said opposed ends, said outer O-ring having surface means formed integral therewith for overlapping the outer edge of the wound, said surface means on said outer O-ring including opposed substantially flat surfaces for enabling tactile gripping and rolling of said sleeve onto said outer O-ring and rolling the remaining lengthwise portion of the sleeve on itself about the outer O-ring to shorten the sleeve in predetermined increments and to resist subsequent lengthening, whereby the sleeve length can be adjusted before or after placement in the wound.

2. An adjustable surgical wound protector according to claim 1 wherein:

said opposed surfaces lie in parallel planes perpendicular to a lengthwise extension of said sleeve to provide said outer O-ring with an oblate cross-section.

3. An adjustable surgical wound protector according to claim 1, wherein:

each of said opposed surfaces has a width determined substantially by the formula $W=xD$, when W is the width of the flat, x is a constant equal to about 0.85, and D is the diameter of the transverse cross-section of the O-ring.

4. An adjustable surgical wound protector according to claim 3 wherein:

said outer O-ring has a Shore A durometer in a range of about 50 to about 90.

5. An adjustable surgical wound protector according to claim 1 wherein:

said sleeve is of urethane material.

6. An adjustable surgical wound protector according to claim 5 wherein:

said sleeve is a thin sheet disposed in a generally cylindrical form with overlapping lengthwise margins sealed together.

7. An adjustable surgical wound protector according to claim 5 wherein:

said sleeve has a thickness of about 3 mils.

8. An adjustable surgical wound protector according to claim 1 wherein:

said sleeve is seamless.

9. An adjustable surgical wound protector according to claim 1 wherein:

said inner and outer O-rings are of urethane having a durometer in a range of about 50 to about 90 Shore A.

10. An adjustable surgical wound protector according to claim 9 wherein:

said inner O-ring material has a hardness in a range of about 70 to about 80 Shore A durometer.

11. An incrementally adjustable surgical wound protector comprising:

an elongate sleeve of flexible material open at opposed ends;

a first resilient ring secured around one of said ends deformable into an oblong shape for insertion with a portion of said sleeve into a wound and formed to expand against the inner edge of the wound; and a second resilient ring secured around the other of said sleeve ends and formed with an oblate cross-section having opposed chordal surfaces for enabling the gripping and rolling of a remaining portion of said sleeve in increments on itself and against the outer edge of the wound, whereby the sleeve length may be adjusted in increments either before or after placement in the wound.

12. An incrementally adjustable surgical wound protector according to claim 11 wherein:

said chordal surfaces are disposed transverse to the length of said sleeve in both an as-manufactured condition and an incrementally-adjusted condition.

13. An incrementally adjustable surgical wound protector according to claim 12 wherein:

said chordal surfaces are flat and are located in parallel planes equidistant from the centroid of said cross-section.

14. An incrementally adjustable surgical wound protector according to claim 13 wherein:

said parallel planes are perpendicular to the central longitudinal axis of the sleeve.

15. An incrementally adjustable surgical wound protector according to claim 13 wherein:

said sleeve is a thin sheet of generally cylindrical form wrapped about said rings and secured thereto.

16. An incrementally adjustable surgical wound protector according to claim 11 wherein:

each of said rings is of urethane having a hardness in a range of about 50 to about 90 Shore A scale.

17. An incrementally lengthwise adjustable wound protector for use in surgery comprising:

a elongate flexible sleeve open at opposite ends, an inner ring secured to said sleeve at one end, an outer ring secured to said sleeve at the opposite end, said outer ring having an oblate transverse cross-section defined by a diametrically opposed pair of accurate surfaces interconnected by an opposed pair of chordal surfaces, said chordal surfaces extending outwardly from said sleeve in a plane perpendicular to a central axis extending lengthwise of said sleeve, said outer ring being in a minimally strained stable condition when said chordal surfaces are lying in said plane, said outer ring being operable, when rolled 180° about its centroid, to roll said sleeve about itself and thereby to adjust the length of the sleeve in increments.

18. An incrementally adjustable wound protector according to claim 17 wherein at least said outer ring is of urethane having a durometer in a range of about 50 to about 90 Shore A.

19. An incrementally adjustable wound protector according to claim 17 wherein the chordal width of each chordal surface is defined substantially by the formula: $W=xD$, wherein W is the width, x is a constant of 0.85, and D is the diametrical distance between said arcuate surfaces.

* * * * *

UNITED STATES PATENT AND TRADEMARK OFFICE
CERTIFICATE OF CORRECTION

PATENT NO. : 5,524,644
DATED : June 11, 1996
INVENTOR(S) : Berwyn M. Crook

It is certified that error appears in the above-indentified patent and that said Letters Patent is hereby corrected as shown below:

Claim 5, line 3, "urethane" should read --polyolefin--.

Signed and Sealed this

Seventh Day of October, 1997

Attest:

BRUCE LEHMAN

*Attesting Officer*  *Commissioner of Patents and Trademarks*